(12) United States Patent
     Simard

(10) Patent No.: US 10,202,449 B2
(45) Date of Patent: *Feb. 12, 2019

(54) CACHEXIA TREATMENT

(71) Applicant: XBiotech, Inc., Vancouver (CA)

(72) Inventor: John Simard, Austin, TX (US)

(73) Assignee: XBIOTECH, INC., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/730,218

(22) Filed: Oct. 11, 2017

(65) Prior Publication Data

US 2018/0037647 A1    Feb. 8, 2018

Related U.S. Application Data

(63) Continuation of application No. 13/624,004, filed on Sep. 21, 2012, now Pat. No. 9,809,649.

(60) Provisional application No. 61/538,309, filed on Sep. 23, 2011.

(51) Int. Cl.
    *C07K 16/24*   (2006.01)
    *A61K 39/00*   (2006.01)
    *A61K 39/395*  (2006.01)

(52) U.S. Cl.
    CPC .......... *C07K 16/245* (2013.01); *A61K 39/395* (2013.01); *A61K 2039/505* (2013.01); *C07K 2317/76* (2013.01)

(58) Field of Classification Search
    CPC .............. C07K 16/245; C07K 2317/76; A61K 39/3955; A61K 39/395; A61K 2029/505
    See application file for complete search history.

(56) References Cited

U.S. PATENT DOCUMENTS

2010/0221179 A1*  9/2010  Hsieh ................... A61K 45/06
                                                    424/1.49

OTHER PUBLICATIONS

Dinarello, C.A. Biologic basis for Interleukin-1 in disease. Blood, 1996, vol. 87, No. 6, p. 2095-2147.*
Oldenberg, H.S.A., et al. Cachexia and the acute-phase protein response in inflammation are regulated by interleukin-6. Eur. J. Immunol., 1993, vol. 23, p. 1889-1894.*

* cited by examiner

*Primary Examiner* — Robert S Landsman
*Assistant Examiner* — Bruce D. Hissong
(74) *Attorney, Agent, or Firm* — Stanley A. Kim

(57) ABSTRACT

Administration of an antibody that specifically binds IL-1α is useful for treating cachexia and increasing the lifespan of a subject suffering from cachexia.

3 Claims, 1 Drawing Sheet

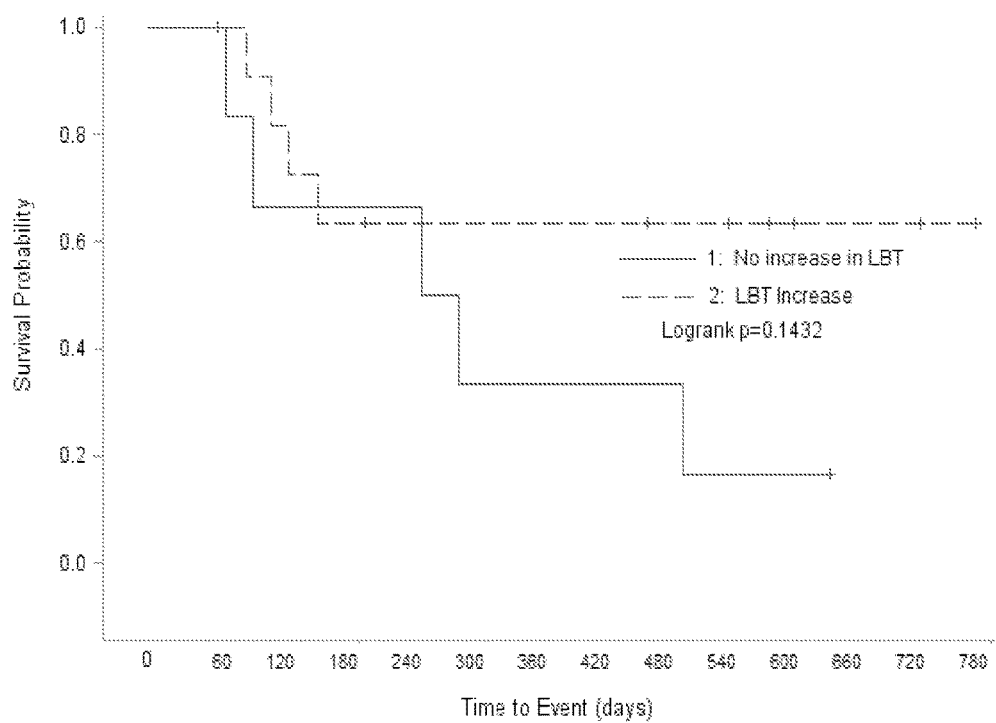

CACHEXIA TREATMENT

CROSS-REFERENCE TO RELATED APPLICATIONS

This application is a continuation application of U.S. nonprovisional patent application Ser. No. 13/624,004 filed on Sep. 21, 2012, which claims priority from U.S. provisional patent application No. 61/538,309 filed on Sep. 23, 2011.

FIELD OF THE INVENTION

The invention relates generally to the fields of medicine, oncology, metabolism, and immunology. More particularly, the invention relates to the use of agents such as antibodies (Abs) which specifically bind interleukin-1α (IL-1α) to treat one or more symptoms of cachexia.

BACKGROUND

Cachexia is a condition characterized by weight loss, muscle atrophy, anorexia, fatigue, and weakness. It is commonly seen in patients with chronic progressive diseases such as AIDS, hormone deficiency, chronic obstructive lung disease (COPD), congestive heart failure (CHF), tuberculosis (TB), and cancer. In cachexia, a decline in food intake relative to energy expenditure leads to weight loss. Even with adequate nutritional support, abnormalities in the metabolism of carbohydrates, proteins, and fats causes continued mobilization and ineffective repletion of host tissue. The physiological mechanisms that cause cachexia remain poorly understood, although cachectin/TNF or other inflammatory cytokines have been implicated.

Nutritional support can help maintain the body weight of cachectic patients, but does not prevent loss of lean muscle mass. Steroids (particularly progesterone-like drugs) can increase appetite and reverse weight loss, although again there is no evidence that it reverses the loss of muscle mass. A humanized anti-IL-6 antibody was evaluated as a treatment for cachexia in a clinical trial involving lung cancer patients. The antibody appeared to be safe and well tolerated, improved the lung symptom score, reversed fatigue, and reduced the rate of lean body mass loss. It did not, however, reverse this process.

SUMMARY

The invention is based on the discovery that an agent that specifically target IL-1α can improve the symptoms of cachexia in human patients—including reversing the loss of lean body mass (or lean body tissue; LBT) and increasing the survival of cancer patients having a loss of lean body mass associated with cachexia. The is believed to be the first showing that a cytokine-targeting agent can increase lean body mass in a human subject with cachexia and increase the survival of cancer patients having a loss of lean body mass associated with cachexia.

Accordingly, the invention features a method of treating cachexia in a human subject by administering to the subject a pharmaceutical composition including a pharmaceutically acceptable carrier and an amount of an IL-1α-targeting agent effective to ameliorate a symptom of cachexia. Also within the invention is a method of extending the survival of a human subject with cachexia by administering to the subject a pharmaceutical composition including a pharmaceutically acceptable carrier and an amount of an IL-1α-targeting agent effective to extend the survival of the subject.

The IL-1α-targeting agent can be an anti-IL-1α Ab such as a anti-IL-1α monoclonal Ab (mAb). The anti-IL-1α Ab can be the mAb designated as MABp1 (see U.S. patent application Ser. No. 13/225,029 filed Sep. 2, 2011 for a description of this antibody) or a mAb that includes one or more complementarity determining regions (CDRs) of MABp1.

The pharmaceutical composition can be administered to the subject by injection, subcutaneously, intravenously, or intramuscularly. In the method, the dose administered to the patient can be at least 0.05 (e.g., at least 0.05, 0.10, 0.25, 0.5, 0.75, 1, 2, 3, 4, or 5) mg/kg of body weight.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27$^{th}$ Edition, Lippincott, Williams & Wilkins, 2000.

As used herein, an "Ab" or "Ab" is an immunoglobulin (Ig), a solution of identical or heterogeneous Igs, or a mixture of Igs. An "Ab" can also refer to fragments and engineered versions of Igs such as Fab, Fab', and F(ab')$_2$ fragments; and scFv's, heteroconjugate Abs, and similar artificial molecules that employ Ig-derived CDRs to impart antigen specificity. A "mAb" or "mAb" is an Ab expressed by one clonal B cell line or a population of Ab molecules that contains only one species of an antigen binding site capable of immunoreacting with a particular epitope of a particular antigen. A "polyclonal Ab" or "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule.

A "therapeutically effective amount" is an amount which is capable of producing a medically desirable effect in a treated animal or human (e.g., amelioration or prevention of a disease or symptom of a disease, or extension of survivability or lifespan).

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DESCRIPTION OF THE DRAWING

FIG. 1 is a Kaplan-Meier curve showing survival among patients with screening and follow up DEXA (n=18) according to evidence of LBT increase.

DETAILED DESCRIPTION

The invention encompasses compositions and methods for ameliorating one or more symptoms of cachexia in a subject and/or extending the survival of a subject having cachexia. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008

Treatment of Cachexia

The compositions and methods described herein are useful for treating cachexia in a mammalian subject by administering to the subject a pharmaceutical composition including an amount of an IL-1α-targeting agent effective to improve at least one characteristic of cachexia in the subject, and/or to extend the survival of a mammalian subject with cachexia (particularly cancer-associated cachexia). The mammalian subject might be any that suffers from cachexia including, human beings, dogs, cats, horses, cattle, sheep, goats, and pigs. Human subjects might be male, female, adults, children, or seniors (65 and older). The mammalian subject can be one with cancer (particularly metastatic cancer; solid tumor cancers; and stage II, III, or IV cancers), HIV infection, TB, COPD, CHF, chronic renal failure, a hormone imbalance, severe trauma (e.g., burns), hypermetabolism (e.g., sustained elevated heart rate of at least 6 bpm over normal for a given subject), excessive sympathetic nerve activity, a hyper-inflammatory state (e.g., elevated CRP levels, increased IL-6 levels, increased TNFα levels, and/or increased IFNγ levels), a >51b weight loss in the preceding 2 months, and/or an estimated daily caloric intake of <20 cal/kg. Subjects with cancer can be those with an expected lifespan of less than 24, 18, 12, or 6 months). The subject may also be on that is being or has been treated with steroids, nutritional supplements, and/or appetite stimulants.

Any symptom of cachexia susceptible to amelioration by administration of an IL-1α targeting agent might be targeted. Examples of such symptoms include weakness, fatigue, gastrointestinal distress, sleep/wake disturbances, pain, listlessness, shortness of breath, lethargy, depression, malaise, anorexia, weight loss, muscle atrophy, and loss lean body mass. The improvement, if measureable by percent, can be at least 1, 2, 3, 4, 5, 10, 15, 20, 25, 30, 40, 50, 60, 70, 80, or 90%. Symptoms such as weakness, fatigue, pain, listlessness, depression, and malaise can be measured by techniques known in the art (e.g., using tests such as EORTC-global quality of life, the Beck Depression Inventory, the Zung Self-rating Depression Scale, the Center for Epidemiologic Studies-Depression Scale, the Hamilton Rating Scale for Depression, and patient self-reporting). For assessing anorexia, muscle mass, or lean body mass assessment, dual-emission X-ray absorptiometry scan (DEXA), bioelectrical impedance analysis (BIA), indirect calorimetry, nutrition diaries, and similar known methods can be used.

The extension of survival of a mammalian subject with cachexia can be at least 10, 20, 30, 40, 50, 60, 70, 80, 90, 100, 150, or 200% over the expected lifespan of the subject. The expected lifespan of a subject with a particular disease associated with cachexia can be calculated by known methods, e.g., by averaging historical data. Expected survival times in cancer patients can be determined by known methods, e.g., as described in Llobera et al., Eur. J. Cancer, 36:2036, 2000 and McCusker et al., J. Chron. Dis., 37:377, 1984.

Antibodies and Other Agents that Target IL-1α

Any suitable type of Ab or other biologic agent (e.g., a fusion protein including an IL-1α-binding component such as an IL-1 receptor) that specifically binds IL-1α and reduces a characteristic of cachexia in a subject and/or extends the survival of a mammalian subject with cachexia might be used in the invention. For example, the anti-IL-1α Ab used might be mAb, a polyclonal Ab, a mixture of mAbs, or an Ab fragment or engineered Ab-like molecule such as an scFv. The Ka of the Ab is preferably at least $1 \times 10^9$ M$^{-1}$ or greater (e.g., greater than $9 \times 10^{10}$ M$^{-1}$, $8 \times 10^{10}$ M$^{-1}$, $7 \times 10^{10}$ M$^{-1}$, $6 \times 10^{10}$ M$^{-1}$, $5 \times 10^{10}$ M$^{-1}$, $4 \times 10^{10}$ M$^{-1}$, $3 \times 10^{10}$ M$^{-1}$, $2 \times 10^{10}$ M$^{-1}$, or $1 \times 10^{10}$ M$^{-1}$). In a preferred embodiment, the invention utilizes a fully human mAb that includes (i) an antigen-binding variable region that exhibits very high binding affinity (e.g., at least nano or picomolar) for human IL-1α and (ii) a constant region. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 mAb described in U.S. patent application Ser. No. 12/455,458 filed on Jun. 1, 2009. Other useful mAbs are those that include at least one but preferably all the CDRs of MABp1. CDRs may be determined according to known methods such as described in Ofran et al., J. Immunol., 181:6230, 2008; and *Antibody Engineering Volume* 2, 2d edition, Konterman and Dubel (eds), Springer, 2010.

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects are screened for the presence of such human IL-1α-specific Ab in their blood. Those subjects that express the desired Ab can then be used as B lymphocyte donors. In one possible method, peripheral blood is obtained from a human donor that possesses B lymphocytes that express human IL-1α-specific Ab. Such B lymphocytes are then isolated from the blood sample, e.g., by cells sorting (e.g., fluorescence activated cell sorting, "FACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, Monoclonal Antibodies: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and *E. coli* cells). Because Igs include heavy (H) and light (L) chains in an $H_2L_2$ configuration, the genes encoding each may be separately isolated and expressed in different vectors.

Although generally less preferred due to the greater likelihood that a subject will develop an anti-Ab response, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. See, e.g., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, mAbs with a desired binding specificity can be humanized by various vendors or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs.

While the IL-1α specific Abs described above are preferred for use in the invention, in some cases, other agents that specifically target IL-1α might be used so long as their administration leads to improvement of a characteristic of cachexia. These other agents might include small organic molecules, aptamers, peptides, and proteins that specifically bind IL-1α (e.g., anakinra or rilonacept).

Pharmaceutical Compositions and Methods

The anti-IL-1α Ab compositions may be administered to animals or humans in pharmaceutically acceptable carriers (e.g., sterile saline) that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent).

The Ab compositions may be administered to animals or humans by any suitable technique. Typically, such administration will be parenteral (e.g., intravenous, subcutaneous, intramuscular, or intraperitoneal introduction). The compositions may also be administered directly to a target site by, for example, injection. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti IL-1α Ab compositions is an amount which shows clinical efficacy in patients as measured by the improvement in one or more cachexia characteristics described above. As is well known in the medical arts, dosage for any one animal or human depends on many factors, including the subject's size, body surface area, age, the particular composition to be administered, sex, time and route of administration, general health, and other drugs being administered concurrently. Preferred doses range from about 0.2 to 20 (e.g., 0.05, 0.10, 0.15, 0.2, 0.3, 0.4, 0.5, 1, 2, 3, 4, 5, 6, 7, 8, 9, 10, 15, 20, or 40) mg/kg body weight. The dose may be given repeatedly, e.g., hourly, daily, semi-weekly, weekly, bi-weekly, tri-weekly, or monthly. Preferably 2 or more (e.g., 3, 4, 5, 6, 7, 8, 9, 10 or more) doses are given.

EXAMPLES

Example 1—Xilonix™

Xilonix™ is a sterile injectable liquid formulation of 15 mg/mL MABp1 in a stabilizing isotonic buffer (pH 6.4). Each 10-mL Type I borosilicate glass serum vial contains 4, 5 or 10 mL of the formulation, and is sealed with a 20-mm Daikyo Flurotec butyl rubber stopper and flip-off aluminum seal. The product is stored at 5±3° C., with excursions to room temperature permitted. The exact composition of the drug product is shown below:

| Composition of the Drug Product (Xilonix™) | | | |
|---|---|---|---|
| Ingredient | Grade | Manufacturer | Concentration |
| MABp1 Ab | GMP | XBiotech | 15 mg/mL |
| sodium phosphate dibasic | compendial | J T Baker | 12 mg/mL |
| citric acid monohydrate | compendial | J T Baker | 2 mg/mL |
| Trehalose•2H2O (high-purity low endotoxin) | compendial | Ferro-Pfanstiehl | 60 mg/mL |
| polysorbate 80 | compendial | J T Baker | 0.2 mg/mL |

| Composition of the Drug Product (Xilonix™) | | | |
|---|---|---|---|
| Ingredient | Grade | Manufacturer | Concentration |
| Phosphoric acid, to adjust pH | compendial | J T Baker | 0.04 mg/mL |
| water for injection | compendial | Microbix | q.s. |

Method of Administration:

The calculated volume is withdrawn from the drug (mAb)-containing vial(s) using a suitable syringe. The drug is then injected into a small IV bag containing 100 mL of normal saline (0.9% NaCl) and mixed by inversion. The diluted drug product can be stored at room temperature for 3 hours prior to administration and is infused over a 1-hour period, with the subject being monitored for signs of an infusion reaction. The infusion is chased with a minimum of 30 mLs of normal saline to deliver any product that may be held up in the infusion set.

Example 2—Improvements in Body Composition, Nutritional Intake and Quality of Life in Advanced Cancer Patients on a Phase I Study of MABp1, a Fully Human, Monoclonal Antibody Against the IL-1α

Background: The proinflammatory cytokine IL-1α plays an important role in anorexia-cachexia syndrome, a complex metabolic disorder associated with loss of muscle mass and pathologic inflammatory response. MABp1 is the first fully human monoclonal antibody with high-affinity against IL-1α. The effect of MABp1 on body composition, nutrition intake and quality of life in a cohort of Phase I patients was determined.

Methods: An open label, first-in-man, Phase I trial of MABp1 was conducted in patients with refractory, metastatic disease that had failed a median of 5 regimens of previous therapy. Patients were defined as refractory since they had failed all standard of care therapy and had no remaining therapeutic options that would be expected to provide benefit. Patients were given MABp1 intravenously at one of 4 dose levels (0.25, 0.75, 1.25, 3.75 mg/kg) once every 3 weeks. For anorexia-cachexia assessment, serial data on dual-emission X-ray absorptiometry scan (DEXA), bioelectrical impedance analysis (BIA), indirect calorimetry, nutrition diary, and the European Organization for Research and Treatment of Cancer Quality of Life Questionnaire (EORTC QLQ-C30) were utilized. Body composition, nutritional intake and quality of life was compared between baseline and cycle 3.

Early Results: Baseline characteristics of the 36 enrolled patients were: average age 60, female 20 (56%), colorectal malignancies 14 (40%), median weight 61 kg (interquartile range 57-80 kg), median body mass index 24 (21-29 kg/m²) and 32/33 (97%) were hypermetabolic. Of the 24 patients that were restaged, an overall response rate of 37% (9/24) was achieved according to RECIST criteria (defined as stable disease or better for ≥3 months). Out of these 24, 18 patients complied as scheduled with DEXA scans both at screening and at the 8-week follow-up assessment. Analysis of baseline and follow-up DEXA scans showed the remarkable finding that most patients had a reversal of their cachexia. At follow-up, 67% (12/18) of patients had an objective increase in lean body tissue (LBT). See Table 1 below. Responders showed an average LBT improvement of 1.57±1.95 kg (p=0.017) compared to their baseline values. On the other hand, the average LBT change among the 6 non-responders was −0.82±0.47 kg. The increase in LBT for responders vs. non-responders was 2.39±1.7 kg (p=0.001).

TABLE 1

Dexa Results by Individual Study Subject

| | | | | | Total Lean Body Tissue (kg) | | | |
|---|---|---|---|---|---|---|---|---|
| Subject | Dose | SEX | Cancer Type | Age | Screening | Cycle 3 | Change | % Change |
| 1 | 0.25 mg/kg | Male | Renal Cell | 55 | 55.91 | 54.72 | −1.19 | −2.1% |
| 2 | 0.25 mg/kg | Female | KRAS + CR | 63 | 35.98 | 36.50 | 0.52 | 1.4% |
| 3 | 0.75 mg/kg | Female | Castleman's | 55 | 42.87 | 42.98 | 0.11 | 0.3% |
| 4 | 0.75 mg/kg | Female | Non-small cell | 75 | 37.98 | 40.79 | 2.81 | 7.4% |
| 5 | 0.75 mg/kg | Male | Colorectal | 64 | 57.97 | 59.16 | 1.19 | 2.1% |
| 6 | 1.25 mg/kg | Male | KRAS + CR | 81 | 43.75 | 43.52 | −0.23 | −0.5% |
| 7 | 1.25 mg/kg | Female | KRAS + CR | 58 | 28.84 | 31.06 | 2.22 | 7.7% |
| 8 | 3.75 mg/kg | Female | Non-small cell | 83 | 36.23 | 35.67 | −0.57 | −1.6% |
| 9 | 3.75 mg/kg | Male | Rectal | 72 | 49.82 | 50.31 | 0.48 | 1.0% |
| 10 | 3.75 mg/kg | Male | Medullary Thyroid | 48 | 48.17 | 46.77 | −1.40 | −2.9% |
| 11 | 3.75 mg/kg | Male | Neuroendocrine | 65 | 56.71 | 63.64 | 6.93 | 12.2% |
| 12 | 3.75 mg/kg | Female | KRAS + CR | 58 | 25.02 | 27.74 | 2.73 | 10.9% |
| 13 | 3.75 mg/kg | Female | Colorectal KRAS+ | 62 | 35.80 | 35.09 | −0.72 | −2.0% |
| 14 | 3.75 mg/kg | Female | Pseudomyxoma peritonei | 60 | 48.96 | 49.29 | 0.32 | 0.7% |
| 15 | 3.75 mg/kg | Male | EBV + NPC | 44 | 53.10 | 53.12 | 0.02 | 0.0% |
| 16 | 3.75 mg/kg | Female | Follicular Thyroid | 50 | 27.34 | 28.12 | 0.78 | 2.8% |
| 17 | 3.75 mg/kg | Female | Adenoid CA of Lung | 52 | 40.54 | 39.84 | −0.70 | −1.7% |
| 18 | 3.75 mg/kg | Female | Breast | 54 | 36.86 | 37.62 | 0.76 | 2.1% |

Conclusions: A reversal of LBT loss is not known to occur in patients with refractory metastatic disease. There are no reports in the literature of an agent able to facilitate increases in LBT in refractory metastatic disease. In the current study, most patients that entered study had dramatic loss in body weight prior to enrollment. Nonetheless, several of the responders, gained enough LBT over the 8 week treatment to result in higher body weight than what was observed 26 weeks prior to start of study.

Interestingly, those patients that gained LBT during treatment also on average lost 0.4 kg of fat mass. The gain of lean body tissue with concurrent loss of fat mass is highly suggestive of a profound change in the control of metabolic energy use—from mobilization of muscle as an energy source, to the utilization of fat and synthesis of muscle tissue.

Other results: 7/14 (50%) patients with BIA data also had an increase in muscle mass (median 1.4 kg, Q1-Q3 1.1-1.8 kg). The daily average caloric intake increased in 8/13 (62%) patients by a median of 362 kcal (Q1-Q3 234-922 kcal). Between baseline and cycle 3, EORTC-Appetite improved in 5/20 (25%) patients (median improvement 33/100, Q1-Q3 33-33) and stayed the same in the remaining 15/20 (75%) patients. EORTC-global quality of life improved in 7/20 (36%) (median improvement 20/100, Q1-Q3 8-25) and remained the same in 8/20 (40%) patients.

Example 3—Analysis of Colorectal Cohort

The majority of patients enrolled and treated in the trial described in Example 2 had refractory metastatic colorectal cancer (14 out of 42). Out of the 18 subjects evaluated with DEXA, 7 had metastatic colorectal carcinoma, and 5 of these 7 responded with an increase in LBT. The average increase in LBT for all 7 of these subjects was 3%, and for those who responded the average increase was 4.6%. Subjects enrolled in this trial were also evaluated for tumor response using RECIST 1.1. Because of this, some subjects were discontinued due to radiographic evidence of disease progression. Among the 14 subjects with colorectal carcinoma, the median duration of survival was 129 days (4.3 months), with 4 of these data points having been censored. For the 10/14 (71%) patients who received at least 3 doses of study drug, the median survival duration was 224 days (7.5 months). The median survival duration also correlated strongly with an increase in LBT. For the 5 (36%) patients who had objective evidence of an increase in LBT from baseline to week 8, the median survival duration was 474 days (15.8 months). On the other hand, the 9 who showed no evidence of LBT increase only showed a median survival of 72 days (2.4 months). Based upon studies done in similar populations, the expected overall survival for refractory colorectal patients is approximately 4.6 months (Jonker, D., et al. Cetuximab for the Treatment of Colorectal Cancer. N Engl J Med 2006; 357:2040-8).

Example 4—Summary of Survival Results at a Later Time Point

A total of 42 patients (57% female, median age 61 years) with advanced cancer, refractory to a median of 5 previous systemic chemotherapy regimens were enrolled in the study described in Example 2. Colorectal carcinoma was found to be the most common malignancy accounting for a third (14/42) of the total study population. While 23 (55%) patients had completed 3 or more cycles, baseline and end-of-cycle 3 DEXA measurements were available for 18 patients. A total of 18/42 (43%) deaths were reported by the date of analysis. The average survival duration was 278±38 days with a median survival of 161 days.

Example 5—Survival in Responders Vs. Non-Responder

In the study described in Example 2, a total of 18 patients had DEXA measurement available at screening and at cycle 3 day 15, out of which 12/18 (67%) were responders (≥0 kg LBT change). As shown in FIG. 1, the overall survival duration among the responders was 377±286 (median 339) days and 313±226 (median 277) days for non-responders. In the responder group 8 patients were censored and 4 deaths occurred. Among the non-responders 5/6 patients died (log-rank p=0.143).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising the step of repeatedly administering to a human subject having a loss of mean body mass caused by a chronic disease an agent which targets interleukin-1 alpha (IL-1α) at least until the subject's lean body mass is increased, wherein the agent which targets IL-1α is an anti-IL-1α antibody.

2. The method of claim 1, wherein the antibody is a monoclonal antibody.

3. The method of claim 2, wherein the monoclonal antibody is an IgG1.

* * * * *